US006423210B1

(12) United States Patent
Jalbert et al.

(10) Patent No.: US 6,423,210 B1
(45) Date of Patent: Jul. 23, 2002

(54) PROCESS FOR DEHYDRATING A MINERAL OIL OR OTHER SOLVENTS FOR THE PREPARATION OF MOISTURE-IN-OIL OR MOISTURE-IN-SOLVENT STANDARDS

(75) Inventors: Jocelyn Jalbert, Repentigny; Roland Gilbert, Boucherville, both of (CA)

(73) Assignee: Hydro-Quebec, Montreal (CA)

( * ) Notice: Subject to any disclaimer, the term of this patent is extended or adjusted under 35 U.S.C. 154(b) by 0 days.

(21) Appl. No.: 08/664,432

(22) Filed: Jun. 18, 1996

(51) Int. Cl.$^7$ ..................... C10G 33/04; C10G 19/073
(52) U.S. Cl. ....................... 208/188; 208/283
(58) Field of Search ................. 208/188, 283

(56) References Cited

U.S. PATENT DOCUMENTS

| | | | |
|---|---|---|---|
| 1,847,968 A | | 3/1932 | Luhrs |
| 2,032,527 A | * | 3/1936 | Cox ............... 208/188 |
| 2,399,192 A | * | 4/1946 | Alexander ............ 196/4 |
| 4,124,834 A | | 11/1978 | Walsh |
| 4,151,256 A | * | 4/1979 | Pedersen ............ 422/102 |
| 4,301,133 A | * | 11/1981 | Hayes ............... 423/442 |
| 4,308,106 A | | 12/1981 | Mannfeld |
| 4,437,082 A | | 3/1984 | Walsh et al. |
| 4,444,159 A | * | 4/1984 | Earl ................... 123/3 |
| 4,557,899 A | * | 12/1985 | Schoonover et al. ...... 422/55 |
| 4,577,978 A | * | 3/1986 | Schneider et al. ........ 374/45 |
| 4,747,960 A | | 5/1988 | Freeman et al. |

OTHER PUBLICATIONS

L. Szepes et al. "A New Analytical Method for the Determination of the Water Content of Transfrmer Oils" (IEEE Transactions on Electrical Insulation, Vo. EI–17 No. 4, Aug. 1982—Sixty–Third Annual International Conference of Doble Clients, Mar. 25–29, 1996, Boston, MA, U.S.A.

* cited by examiner

*Primary Examiner*—Nadine Preisch
(74) *Attorney, Agent, or Firm*—Oblon, Spivak, McClelland, Maier & Neustadt, P.C.

(57) ABSTRACT

An oil, such as a mineral oil, for example, transformer oil, is contacted with calcium carbide and the mixture is stirred until a liquid phase containing less than 1 ppm water and a solid phase containing $Ca(OH)_2$ and unreacted $CaC_2$ are obtained. The oil obtained can be used to give samples of known quantities of water by adding corresponding amounts thereto.

18 Claims, 2 Drawing Sheets

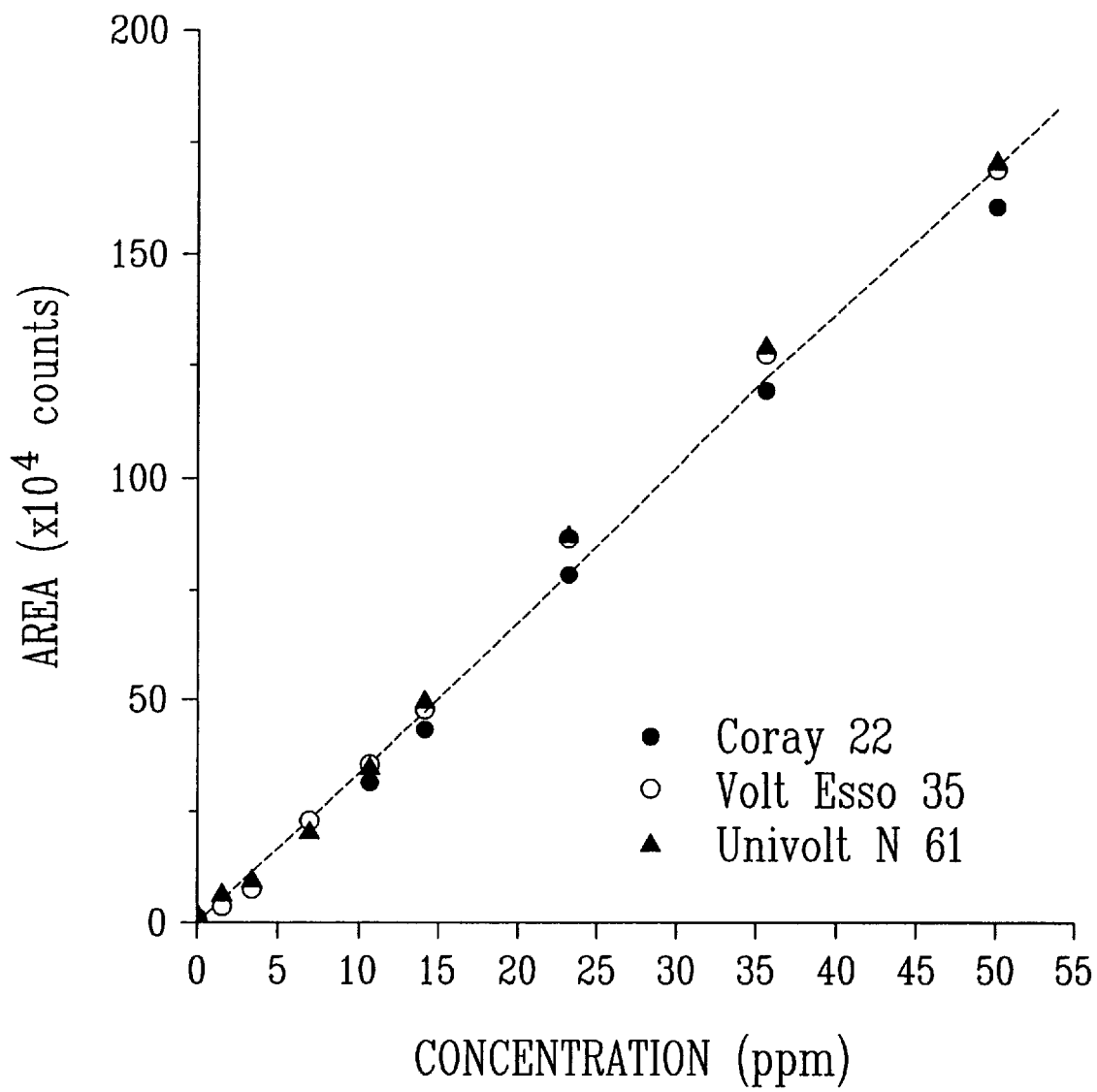

PROCESS FOR DEHYDRATING A MINERAL OIL OR OTHER SOLVENTS FOR THE PREPARATION OF MOISTURE-IN-OIL OR MOISTURE-IN-SOLVENT STANDARDS

BACKGROUND OF INVENTION a) Field of Invention

The present invention relates to, a process for dehydrating a material comprising a mineral oil, aromatic or aliphatic solvents, or the like using calcium carbide. More particularly, the invention relates to the preparation of samples of mineral oil or the like containing a known water concentration.

b) Description of Prior Art

The electrical properties of insulating oils, such as mineral oils, are largely affected by the presence of traces of water, which has led electrical companies to establish maximum admissible water concentrations for insulating oils. In view of this requirement, a monitoring of the water content of insulating oils is carried out so as to detect the cases which require a water removal treatment of the insulating oil. For example, the specification which is presently set by the Applicant for power transformer oils is <10 ppm (w/v) water.

To achieve this, the determination of the water content is carried out by the Karl Fischer's coulometric titration method. Although this method has a lot of merit, since it is reasonably accurate and can be advantageously employed in several fields, it has some drawbacks for this specific application. For example, when the determination is made with an oil which has been exposed to severe electric and thermal effects, the presence of degradation products with unsaturated carbon-carbon bonds which react with iodine through halogen addition causes errors in Karl Fischer's method. In view of the problems associated with the Karl Fischei's method, there is a need for substantially dehydrated oil samples and moisture-in-oil standards to verify the performance of the method.

Another problem with present technology is that the currently used apparatuses for detecting the water content of mineral oils are calibrated from concentrated solutions of water in methanol which could affect the analytical performance. The apparatuses should be normally calibrated in the range of the concentrations experienced with the field samples using standards prepared in the same matrix. For the present application, the oil is the matrix, whereas dissolved water, is the analyte to be determined.

There is therefore a need to obtain an accurate and precise determination of the water content of mineral oils and the like using an apparatus which has been calibrated to less than 1 ppm water with the appropriate standards.

L. Szepes et aL in "A New Analytical Method for the Determination of the Water Content of Transformer Oils" (Transactions on Electrical Insulation, Vol. EI-17 No. 4, August 1982) describe a method based on the mass spectrometric determination of HD formed by reacting water with $LiAID_4$. This analytical procedure which implies the removal of water via the above reaction does not refer to the use of calibration standards. Furthermore, it can only dry the oil down to 5 ppm.

On the other hand, U.S. Pat. No. 4,308,106 discloses that it is known to add inter alia calcium carbide in the reflux of glycerin to dehydrate same by the process of U.S. Pat. No. 1,459,699. However, no indication is given that a dehydration to less than 1ppm is possiblebythat method. Also there is no teaching relating to reducing the amount of water in transformer oil below the ppm level. This patent finds application mainly in the production of ethyl alcohol, but none to the treatment of oil.

U.S. Pat. No. 4,747,960 discloses the removal of water from a dielectric oil using a water absorbent polymer, a carboxymethyl cellulose or sodium poly-2-propenoate. However, there is no indication that water removal is possible down to sub-ppm quantities. The method deals with an absorption phenomenon and does not involve chemical reaction.

Another method of demoisturizing is disclosed in U.S. Pat. No. 4,437,082, which uses a desiccant resin. The latter presumably dries a dielectric liquid to 20 ppm or less although no showing is given to support demoistuzing at less than 20 ppm. The only dessicant material disclosed is drying resin HCR-W2. Furthermore, the patent mainly aims at decontaminating a dielectric fluid rather than essentially demoisturizing to very low levels.

U.S. Pat. No. 4,124,834 teaches the removal of a contaminant from an insulating liquid using an adsorbent material. The invention is mainly aimed at removing PCBs, and has nothing to do with the present invention.

U.S. Pat. No. 1,847,968 discloses treating alcohol with quicklime to remove water. There is no teaching relating to reducing the amount of water in transformer oil below the ppm level.

It will therefore be seen that with respect to producing mineral oil or the like which is free of water to a range below one part per million, the prior art is of no help.

It is therefore an object of the present invention to provide a method which enables to produce a sample of a material comprising a mineral oil, aromatic or aliphatic solvent, or the like which is demoisturized to the extent that it can be used to calibrate an apparatus adapted to determine the content of water in the material.

SUMMARY OF INVENTION

According to the invention there is provided a process for dehydrating a material comprising a mineral oil, aliphatic or aromatic solvent or the like, which comprises contacting the material with particulate calcium carbide, under conditions effective to form a liquid phase consisting of dehydrated material substantially free of water and a solid phase comprising calcium hydroxide and unreacted calcium carbide, and separating the liquid phase from said solid phase to give a substantially dehydrated material.

Although the invention may be used with a variety of liquids, it is preferably carried out with transformer oils.

According to the invention, it is possible to calibrate an apparatus for detecting the presence of water in a material such as mineral oil or an aromatic or aliphatic solvent, with the substantially dehydrated material obtained by the process of the invention.

According to a preferred embodiment calcium carbide which has been previously crushed is preferred and the process is normally carried out under anhydrous atmosphere, for example, in a glove box.

According to another preferred embodiment, transformer oil and crushed calcium carbide are introduced in centrifugal bottles, for example, bottles made of polyethylene which are closed using polyethylene screw caps. The bottles are preferably shaken mechanically (Glas-col bench-top shaker, Terre Haute, Ind., USA, equipped with centrige-tube holder) for at least about 60 minutes, and placed in an ultracentrifuge (IEC Centra-MP4, Needham Heights, Mass., USA) to separate said liquid phase from said solid phase. The ultra-centrifuge may operate at a speed of about 13000 rpm for about 5 minutes.

According to yet another embodiment, the bottles are thereafter reintroduced in the glove box and the liquid phase comprising dehydrated oil is then decanted in additional polyethylene bottles. These additional bottles containing dehydrated oil are preferably subjected to at least two additional ultra-centrifugations to separate any remaining solid phase therefrom, and the dehydrated oil is transferred in glass bottles or syringes.

According to yet another preferred embodiment, known amounts of water are introduced into the dehydrated oil present in the glass bottles or glass syringes to produce an oil containing a known concentration of water. Each polyethylene bottle normally contains an excess of calcium carbide, such as 1 g of $CaC_2$ per 4 mL of oil.

DESCRIPTION OF PREFERRED EMBODIMENTS

Samples containing different known amounts of water are required to check the accuracy and precision of apparatuses such as the Karl Fischer device or a device of the type HS/GC (A New Analytical Method for the Determination of Moisture in Transformer Oil Samples, J. Jalbert S. Charbonneau and R. Gilbert, Sixty-Third Annual International Conference of Doble Clients, Mar. 25–29, 1996, Boston, Mass., U.S.A.). To achieve this, it is necessary to have samples of substantially completely dehydrated oil and other samples containing known amounts of water both of which are not available on the market, and which makes it possible to calibrate and verify the analytical performance of measuring instruments.

In order to test the exactness of the process according to the invention in producing substantially completely dehydrated oils, 40 samples, each containing about 40 mL of Volt Esso 35 oil which have been dehydrated by the process of the invention, were prepared. An initial amount of 20 ppm of water was determined in this insulating oil before application of the process.

BRIEF DESCRIPTION OF DRAWINGS

In the drawings which illustrate the invention:

FIG. 2: is a HS/GC calibration graph obtained with water-in-oil standards prepared according to the invention (from Jalbert et al.).

Figure 1:
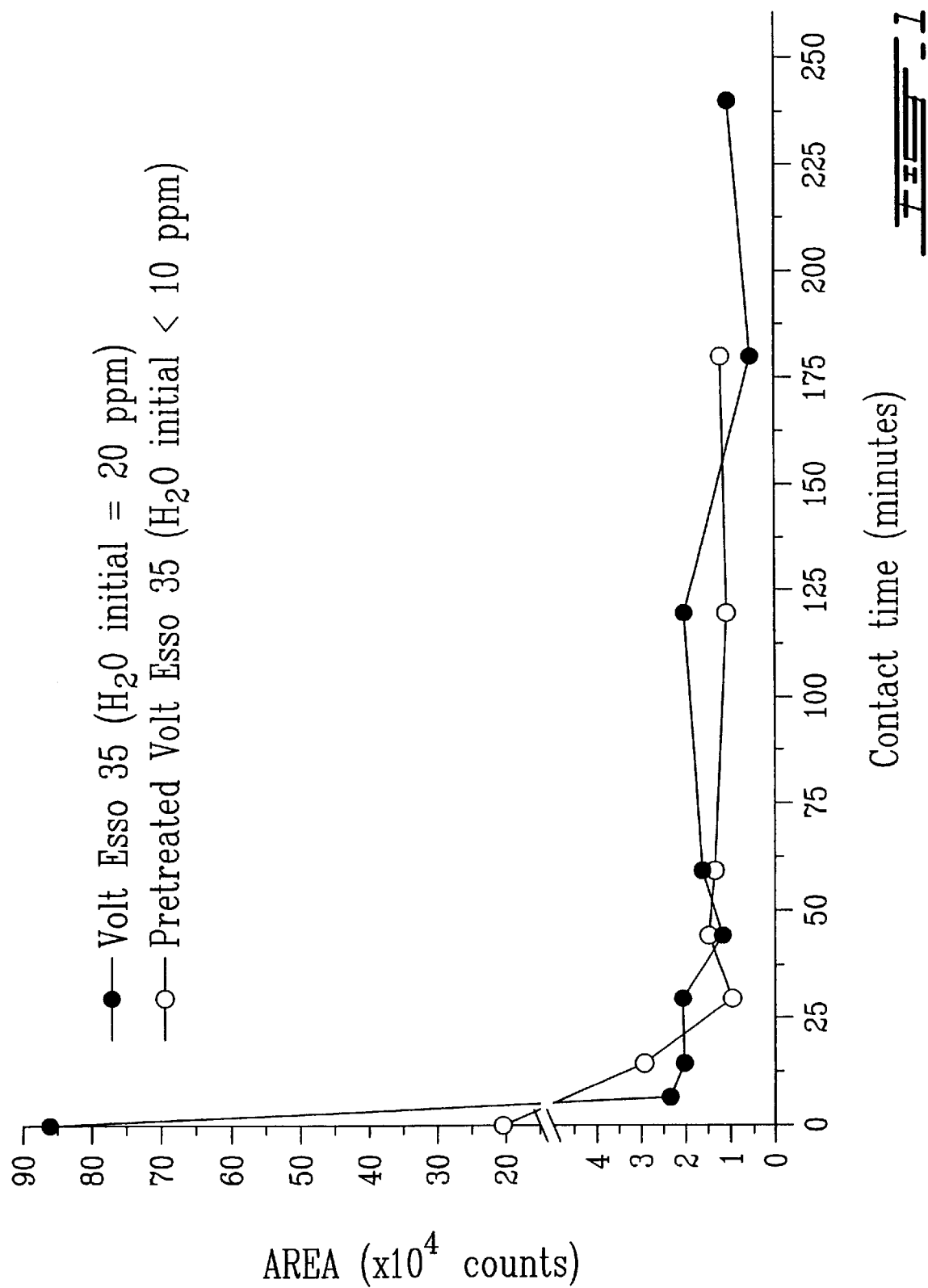
FIG. 1: is a representative of the kinetics of the reaction of water with $CaC_2$ in an oil matrix.

The preparation was as follows. 10 g of previously crushed calcium carbide were first introduced into each of a series of 40 mL centrifugal polyethylene bottles, which were thereafter filled to 40 mL with Volt Esso 35 oil, the preparation being carried out in a glove box. The bottles were removed from the glove box and shaked mechanically for at least 60 minutes. It is believed that as soon as there is contact between the oil and calcium carbide, as well as during the entire shaking period, the following known reaction enables to free the oil from traces of water.

$$CaC_2 \text{ (solid)} + 2H_2O \text{ (oil)} \rightarrow Ca(OH)_2 \text{ (solid)} + C_2H_2 \text{ (gas)}$$

The kinetics of the demoisturizing reaction with the Volt Esso 35 oil is shown in FIG. 1 (filled circles). The water is almost completely removed from the oil after 50 minutes of phases in contact. Another example involving the use of a commercially pretreated Volt Esso 35 sample supplied by Syprotec Inc., Montreal, CA (certified $H_2O$<10 ppm) is also shown in FIG. 1 (open circles).

The by-products of the reaction are in suspension in the oil, in the case of $Ca(OH)_2$, and are partly dissolved in the oil and partly in the gaseous atmosphere of the void above the oil, in the case of $C_2H_2$.

After shaking, the bottles were placed in an ultra-centrifugation device referred to above so as to separate the liquid phase consisting of dried oil and the solid phase consisting of a mixture of calcium hydroxide and unreacted calcium carbide. The ultra-centrifugation device was used at a speed of 13000 rpm for 5 minutes.

A first step of recovery of dried oil was carried out by reintroducing the bottles in the glove box and decanting the oil contained therein into other polyethylene bottles. This operation is repeated twice under the same conditions as previously. After the third centrifugation, the bottles were reintroduced into the glove box and the oil was transferred into glass bottles, which were provided with perforated aluminum. caps fitted with a rubber PTFE-fined septum. At this stage, the product was a dried oil in which the water concentration was always lower than 1 ppm as shown in Table I. The amount of water was assessed using the technique published above by Jalbert et al.

Samples of oil with known water concentrations were prepared by introducing in the dehydrated oil, a known volume (0.5–30 μL) of an Aquatest water standard of 2.70≅0.05% water in methanol (Photovolt, Indianapolis, Ind., USA) using an automatic syringe. The results are given in Table II.

TABLE I

Degree of dehydration after adding Volt Esso 35 oil to 10 g of crushed $CaC_2$ (total volume = 40 mL, contact time = 60 minutes)

| | | Measured Concentration (ppm w/v) | |
| --- | --- | --- | --- |
| Test | Area of peak (counts) | Estimated from the peak area of a standard of 2.86 ppm | Estimated from the peak area of a standard of 9.2 ppm |
| 1 | 10494 | 0.22 | 0.25 |
| 2 | 13562 | 0.28 | 0.32 |
| 3 | 15871 | 0.33 | 0.37 |
| 4 | 16163 | 0.34 | 0.38 |
| 5 | 20800 | 0.43 | 0.49 |
| 6 | 24000 | 0.50 | 0.56 |
| 7 | 21600 | 0.45 | 0.51 |
| 8 | 21700 | 0.45 | 0.51 |
| 9 | 22400 | 0.47 | 0.53 |
| 10 | 9647 | 0.20 | 0.23 |
| 11 | 17276 | 0.36 | 0.41 |
| 12 | 18677 | 0.39 | 0.44 |
| 13 | 19074 | 0.40 | 0.45 |
| 14 | 21353 | 0.45 | 0.50 |
| 15 | 28749 | 0.60 | 0.68 |
| 16 | 19800 | 0.41 | 0.47 |
| 17 | 20800 | 0.43 | 0.49 |
| 18 | 22500 | 0.47 | 0.53 |
| 19 | 19800 | 0.41 | 0.47 |
| 20 | 18677 | 0.39 | 0.44 |
| 21 | 22500 | 0.47 | 0.53 |
| 22 | 9647 | 0.20 | 0.27 |
| 23 | 20800 | 0.43 | 0.49 |
| 24 | 17276 | 0.36 | 0.41 |
| 25 | 19074 | 0.40 | 0.45 |
| 26 | 21353 | 0.45 | 0.50 |
| 27 | 14109 | 0.29 | 0.33 |

TABLE I-continued

Degree of dehydration after adding Volt Esso 35 oil to 10 g of crushed CaC$_2$ (total volume = 40 mL, contact time = 60 minutes)

| Test | Area of peak (counts) | Measured Concentration (ppm w/v) Estimated from the peak area of a standard of 2.86 ppm | Estimated from the peak area of a standard of 9.2 ppm |
|---|---|---|---|
| 28 | 19673 | 0.41 | 0.46 |
| 29 | 21480 | 0.45 | 0.51 |
| 30 | 16315 | 0.34 | 0.38 |
| 31 | 18637 | 0.39 | 0.44 |
| 32 | 20127 | 0.42 | 0.47 |
| 33 | 16879 | 0.35 | 0.40 |
| 34 | 20317 | 0.42 | 0.48 |
| 35 | 17010 | 0.35 | 0.40 |
| 36 | 17874 | 0.37 | 0.42 |
| 37 | 8446 | 0.18 | 0.20 |
| 38 | 11906 | 0.25 | 0.28 |
| 39 | 18309 | 0.38 | 0.43 |
| 40 | 25317 | 0.53 | 0.59 |
| Average value | 18499 | 0.39 | 0.43 |

TABLE II

Addition of a specific volume of a certified water solution in methanol in a sample of 15 mL dried Volt Esso 35 oil

| Test | Expected concentration (ppm w/v) | Measured concentration (ppm w/v) | Accuracy of preparation* % |
|---|---|---|---|
| 1 | 0.9 | 1.1 | −22.2 |
| 2 | 1.7 | 1.7 | −2.4 |
| 3 | 1.8 | 2.0 | −11.1 |
| 4 | 1.8 | 1.6 | 11.1 |
| 5 | 3.4 | 3.1 | 7.7 |
| 6 | 3.4 | 3.1 | 7.7 |
| 7 | 3.6 | 3.9 | −8.3 |
| 8 | 3.6 | 4.3 | −19.4 |
| 9 | 6.7 | 6.6 | 1.5 |
| 10 | 7.2 | 8.0 | −11.1 |
| 11 | 8.4 | 8.4 | 0 |
| 12 | 8.4 | 9.1 | −8.3 |
| 13 | 8.4 | 8.4 | 0 |
| 14 | 8.4 | 8.4 | 0 |
| 15 | 8.4 | 9.1 | −8.3 |
| 16 | 9.0 | 8.4 | 6.7 |
| 17 | 10.8 | 10.8 | 0 |
| 18 | 11.8 | 11.4 | 3.4 |
| 19 | 14.4 | 12.5 | 13.2 |
| 20 | 16.8 | 17.0 | −1.2 |
| 21 | 16.8 | 15.3 | 8.9 |
| 22 | 16.8 | 16.4 | 2.4 |
| 23 | 16.8 | 12.5 | 25.6 |
| 24 | 25.2 | 25.0 | 0.8 |
| 25 | 36.0 | 35.2 | 2.2 |
| 26 | 54.0 | 54.3 | −0.6 |
| 27 | 72.0 | 71.8 | 0.3 |

*Expected concentration - measured concentration × 100 Expected concentration

Of course one of the main values of the process according to the invention is to enable the calibration of devices used to determine water in transformer oils or the like. For example, the calibration of the HS/GC technique referred to above was established by analyzing a series of Toisture-in-oil standards prepared by the procedure according to the present invention. As shown in FIG. 2, standards of 1.8, 3.6, 7.2, 10.8, 14.4, 23.4, 36 and 50.4 ppm water were prepared using three different mineral oil types: Volt Esso 35, Coray 22 and Univolt N 61. It will be seen that the signal passes through zero and increases proportionally with the addition of water in the mineral oil tested, which is a proof of the applicability of the invention.

As shown in Table III, demoisturizing tests according to the invention were also made with aromatic and aliphatic solvents.

TABLE III

Degree of dehydration after adding heptane or benzene to 10 g of crushed CaC$_2$ (total volume = 40 mL, contact time = 60 minutes)*

| Test | Before treatment (ppm w/v) | After treatment (ppm w/v) |
|---|---|---|
| Heptane** | | |
| 1 | 6.7 | <detection limit |
| 2 | 6.1 | 0.38 |
| 3 | 6.7 | 0.50 |
| 4 | 6.7 | 0.46 |
| 5 | 6.7 | 0.54 |
| 6 | 7.7 | 0.42 |
| Benzene*** | | |
| 1 | 191.9 | 3.6 |
| 2 | 168.4 | 3.2 |
| 3 | 180.6 | 2.8 |
| 4 | 192.8 | 2.9 |
| 5 | 176.4 | 2.8 |
| 6 | 179.7 | 2.2 |

*Concentrations assessed by Karl Fischer technique
**HPLC Grade Fisher Chemical with a % water of 0.004
***Certified A.C.S. Fisher Chemical with a % water of 0.03

We claim:

1. A process, which comprises:

providing a material selected from the group consisting of mineral oil, aromatic and aliphatic solvents, said material containing small amounts of water;

contacting said material with previously crushed calcium carbide;

mechanically stirring said calcium carbide with said material thereby causing said calcium carbide to react with water present in said material for a time and under conditions effective to form a liquid phase consisting of said material having a water content less than 0.5 ppm and a solid phase comprising calcium hydroxide and unreacted calcium carbide;

separating said solid phase from said liquid phase;

taking aliquots of said liquid phase to form samples of said material free of said solid phase and containing less than 0.5 ppm water, said samples adapted to constitute standards by adding water to each dehydrated sample to achieve a water concentration level of at least 1 ppm, said standards to be used in a method of determining water content in a given oil or solvent.

2. Process according to claim 1, wherein said material comprises an oil.

3. Process according to claim 1, wherein said material comprises aromatic or aliphatic solvents.

4. The process according to claim 1, which comprises a step of calibrating an apparatus for detecting the presence of water in oil or water in solvent, with said standards.

5. Process according to claim 1, wherein said oil comprises transformer oil.

6. Process according to claim 1, which is carried out under anhydrous atmosphere.

7. Process according to claim 1, wherein said process is carried out in a glove box.

8. Process according to claim 5, wherein said calcium carbide has been crushed in a glove box under an inert atmosphere.

9. Process according to claim 8, wherein said crushed calcium carbide and transformer oil are introduced in centrifugal bottles.

10. The process according to claim 9, wherein said centrifuge bottles are made of a hydrophohic material.

11. Process according to claim 10, which comprises stiring said bottles, and placing said bottles in an ultra-centrige to separate said liquid phase from said solid phase.

12. Process according to claim 9, which comprises operating said ultra-centrige at a speed of about 13000 rpm for about 5 minutes.

13. Process according to claim 12, which comprises reintroducing said bottles in said glove box and thereafter decanting the liquid phase comprising dehydrate oil in additional polyethylene bottles.

14. Process according to claim 13, which comprises subjecting said additional bottles containing dehydrated oil to a second ultra-centrifugation followed by a second decantation, and repeating the latter ultracentrifugation to separate any remaining solid phase therefrom, and transferring the dehydrated oil in glass bottles or glass syringes.

15. Process according to claim 14, which comprises introducing known amounts of water into the dehydrated oil present in said glass bottles to produce an oil containing a known concentration of water.

16. Process according to claim 10, which comprises introducing 10 g of calcium carbide and approximately 40 mL of oil in each said polyethylene bottle.

17. The process according to claim 11, which comprises the step of adding at least 1 ppm water to said samples to constitute said standards.

18. process, which comprises:

providing a quantity of mineral oil containing small amounts of water therein under an inert atmosphere, in a glove box;

introducing in a centrifuge bottle made of hydrophobic material, a sufficient quantity of previously crushed calcium carbide to react with all water present in said mineral oil;

introducing said quantity of mineral oil in said bottle, sealing the same and removing the sealed bottle from the glove box;

mechanically stirring the mixture obtained, for at least about 60 minutes thereby obtaining a liquid phase consisting of said mineral oil in which the water content has been reduced to less than 0.5 ppm and a solid phase comprising calcium hydroxide and unreacted calcium carbide;

placing said seal d bottle in an ultracentrifuge, and operating said ultracentrifuge for at least 5 minutes, thereafter removing said sealed bottle from the ultracentrifuge and introducing it in said glove box and decanting the liquid phase comprising dehydrated mineral oil in an additional centrifuge bottle and sealing same;

removing said additional sealed bottle from said glove box, subjecting said additional bottle containing said dehydrated mineral oil to a second ultracentrifugation followed by a second decantation in said glove box, repeating the latter ultracentrifugation and decantation to separate any remaining solid phase therefrom, and transferring the finally dehydrated oil in a glass bottle or glass syringe to form a sample of mineral oil free of said solid phase and containing less than about 0.5 ppm water, and introducing water into said dehydrated sample to achieve a water concentration level of at least 1 ppm in said sample to constitute a standard to be used in a method of determining water content in a given mineral oil.

* * * * *

UNITED STATES PATENT AND TRADEMARK OFFICE
CERTIFICATE OF CORRECTION

PATENT NO. : 6,423,210 B1
DATED : July 23, 2002
INVENTOR(S) : Jocelyn Jalbert

It is certified that error appears in the above-identified patent and that said Letters Patent is hereby corrected as shown below:

Column 1,
Line 36, "Fischei" should read -- Fischer --;
Line 54, "aL" should read -- al --;
Line 67, "possiblebythat" should read -- possible by that --.

Column 4,
Line 21, "aluminum. caps" should read -- aluminum caps --.

Column 5,
Line 64, "Toisture" should read -- moisture --.

Column 7,
Line 14, "hydrophohic" should read -- hydrophobic --;
Line 17, "centrige" should read -- centrifugation --;
Line 19, "ultra-centrige" should read -- ultra-centrifugation --;
Line 28, "ultracentrifugation" should read -- ultra-centrifugation --.

Column 8,
Line 19, "seal d bottle in an ultracentrifuge" should read -- sealed bottle in an ultra-centrifuge --;
Lines 20 and 21, "ultracentrifuge" should read -- ultra-centrifuge --;
Lines 27 and 29, "ultracentrifugation" should read -- ultra-centrifugation --.

Signed and Sealed this

Twenty-sixth Day of August, 2003

JAMES E. ROGAN
*Director of the United States Patent and Trademark Office*